(12) United States Patent
Karita (10) Patent No.: US 7,104,946 B2
(45) Date of Patent: Sep. 12, 2006

(54) PHYSICAL-HEALTH TUNING MEANS, AND MANUFACTURING AND USE METHODS THEREFOR

(75) Inventor: Masakazu Karita, 39-2 Ooya, Akasaka-cho (JP)

(73) Assignee: Masakazu Karita, Akaiwa ( * ) Notice: Subject to any disclaimer, the term of this patent is extended or adjusted under 35 U.S.C. 154(b) by 120 days.

(21) Appl. No.: 09/682,627

(22) Filed: Oct. 1, 2001

(65) Prior Publication Data

US 2002/0041185 A1 Apr. 11, 2002

(30) Foreign Application Priority Data

Sep. 29, 2000 (JP) .............................. 2000-298524
Feb. 4, 2001 (JP) .............................. 2001-103764

(51) Int. Cl.
*A61B 17/52* (2006.01)
*A61N 2/00* (2006.01)

(52) U.S. Cl. ........................................................ 600/9
(58) Field of Classification Search .................... 600/9, 600/13, 14, 15; 310/198, 181, 68 R; 318/439
See application file for complete search history.

(56) References Cited

U.S. PATENT DOCUMENTS 6,037,692 A * 3/2000 Miekka et al. .............. 310/198
6,132,361 A * 10/2000 Epstein et al. ................ 600/13

* cited by examiner

*Primary Examiner*—Max F. Hindenburg
*Assistant Examiner*—Brian Szmal
(74) *Attorney, Agent, or Firm*—Judge & Murakami IP (57) ABSTRACT

Physical-health tuning means that may adjust and bring into harmony physical health—that in particular may improve physical health out of sorts due to electromagnetic-wave harm—are presented. The physical-health tuning means include: (A) a plurality of bar magnets whose obverse sides are N poles and whose reverse sides are S poles, running lengthwise; (B) wire that is non-magnetic yet electroconductive; and (C) a shaping support material. The wire is arranged coiling the magnet obverse faces in right-hand turns from one end to the other end of the bar magnets in the lengthwise direction. The plurality of magnets onto which the wire is wound are disposed to form a tubular hollow with the N-pole faces adjoining the S-pole faces in alternation, and the shaping support material being put on the outside of this assembly. Combined use with rhombohedral system crystalline substances can increase efficacy.

10 Claims, 7 Drawing Sheets

PHYSICAL-HEALTH TUNING MEANS, AND MANUFACTURING AND USE METHODS THEREFOR

BACKGROUND OF INVENTION

1. Technical Field

The present invention relates to tuning, i.e., adjusting and bringing into harmony, physical health; in particular to means for tuning physical health that is out of sorts due to electromagnetic wave disorders. The invention also relates to methods of manufacturing and to methods of using such physical-health tuning means.

2. Description of Related Art

With the striking spread in recent years of electronic devices such as computers, mobile telephones, microwave ovens, and so forth there is concern over the impact on the human body of electromagnetic waves issuing from these electronic devices.

Electromagnetic wave shielding aprons for shielding from electromagnetic waves issuing from computer cathode-ray tubes are on the market, but are not sufficiently effective in shielding against electromagnetic waves because magnetic fields are not emitted directly from CRT screens, but spiral out from the vertical, describing innumerable ellipses from the emission source.

SUMMARY OF INVENTION

An object of the present invention is to provide an effective physical-health tuning means, as well as a method of manufacturing the physical-health tuning means and a method of using the physical-health tuning means, for persons with complaints that their physical health is out of sorts—particularly persons with complaints that their physical health is out of sorts among persons working in environments in which they are surrounded by electronic devices and are exposed to electromagnetic waves.

Another object is to tune effectively, i.e. adjust and bringing into harmony, the physical health of persons with complaints that their physical health is out of sorts—particularly persons who have such complaints and who work in environments in which they are surrounded by electronic devices and are exposed to electromagnetic waves.

As a result of concerted investigation to attain the foregoing objects, the present invention in a preferred aspect is a physical-health tuning means having: (A) a plurality of bar magnets whose obverse sides are N poles and whose reverse sides are S poles, running lengthwise; (B) wire that is non-magnetic yet electroconductive; and (C) a shaping support material. The physical-health tuning means in a preferred embodiment is characterized in that the wire is arranged coiling the magnet obverse faces in right-hand turns from one end to the other end of the bar magnets in the lengthwise direction; and at the same time, the plurality of magnets onto which the wire is wound are disposed to form a tubular hollow with the N-pole faces adjoining the S-pole faces in alternation, and the shaping support material is put on the outside thereof.

One bar magnet as described at (A) above may alone be used, coiled with wire as described at (B) above, to form a physical-health tuning means in another embodiment of the present invention. The physical-health tuning means herein is thus embodied with no tubular hollow for receiving an insertion body as will be described later.

Alternatively, if bigger-sized bar magnets are used such that their force of magnetic attraction is strong enough to hold the magnets together in the tubular hollow configuration, the shaping support material may not be necessary.

"Right-hand turns" here means the direction following the fingers of the right hand or right-hand threads on a screw.

The bar magnets used in the present invention are magnetized to each have polarity that is divided in the width or thickness direction, rather than the length direction of the magnets. Accordingly, if the bar magnet is as thick as it is wide, the N-pole and the S-pole will lie at once side-by-side and front-to-back on the magnet, the two orientations being indistinguishable. If on the other hand the bar magnets are plate-shaped, the N-poles and the S-poles will be divided front-to-back.

The bar magnets in cross-sectional contour may suitably be rectangular, square, round or elliptical, as long as they form a tubular hollow with the magnets' N-poles and S-poles adjoining each other. As far as forming the hollow space is concerned, a rectangular contour is preferable.

Copper, aluminum, silver, gold, and platinum may be used as the nonmagnetic yet electroconductive wire, or alternatively crystal fiber may be used.

The tubular hollow in the physical-health tuning means is not limited to being round or elliptical in cross-section, but includes tubular hollows from approximately triangular to polygonal in form.

If the number of magnets onto which the wire is wound is three or fewer, form the tubular hollow in the physical-health tuning means would be problematic, so that four or more is preferable.

Further, a left-winding direction to the turns in the wire coils would not be effective; in a preferred embodiment, the coils should have aright-winding direction. Optionally, however, wire-wound magnets coiled with right-hand windings may alternate with magnets coiled with left-hand windings, in the plurality assembled to form a physical-health tuning means under the present invention. The preferable layout arranges one strand of wire in one layer of turns over the magnet obverse face, and over the magnet from the one end to the other end, and makes the gaps where the wire meets itself as small as possible. In this respect, the thickness of the wire may be on the order of 1 mm. The upper limit of the thickness is judged by whether or not the magnets' N-poles and S-poles can attract each other well. Making the physical-health tuning means is problematic and its effects are not gained if the wire is so thick the poles do not attract.

Further, what substance the shaping support material is does not matter as long as it sustains the tubular hollow in, and supports the shape of, the physical-health tuning means. The shaping support material, if it is necessary, may be either cylindrical or strand-like or strap-like, but from a shaping-support and effectiveness/reinforcement standpoint, electroconductive metal wire is preferable. Copper, aluminum, silver, gold, or platinum may be used as the wire material made from a metal having electroconductivity, or alternatively crystal fiber may be used. In this respect, physical-health tuning means of the present invention include a configuration in which one strand of wire continuous and identical with the coiling wire is arranged as the foregoing shaping support material.

The present invention in a further aspect is a method for manufacturing a physical-health tuning means having: (A) a plurality of bar magnets whose obverse sides are N poles and whose reverse sides are S poles, running lengthwise; (B) wire that is non-magnetic yet electroconductive; and (C) a shaping support material; wherein the wire is arranged coiling the magnet obverse faces in right-hand turns from one end to the other end of the bar magnets in the lengthwise direction, and at the same time, the plurality of magnets onto which the wire is wound are disposed to form a tubular hollow with the N-pole faces and the S-pole faces adjoining in alternation, and the shaping support material is put on the outside thereof. The physical-health tuning means manufacturing method manufactures a physical-health tuning means by: arranging the wire by coiling it in right-hand turns on the magnet obverse faces from one end to the other end of the bar magnets in the lengthwise direction; then, disposing the plurality of magnets onto which the wire is coiled to form a tubular hollow with the N-pole faces adjoining the S-pole faces in alternation; and further, putting the shaping support material on the outside thereof.

Herein, the invention in another aspect is the method for manufacturing a physical-health tuning means, in which the invention uses one strand of wire continuous and identical with the coiling wire as the foregoing shaping support material, in which case the shaping and support properties are excellent.

The present invention in a still further aspect is a method for tuning, i.e., adjusting and bringing into harmony, physical health, utilizing a physical-health tuning means having: (A) a plurality of bar magnets whose obverse sides are N poles and whose reverse sides are S poles, running lengthwise; (B) wire that is non-magnetic yet electroconductive; and (C) a shaping support material; wherein the wire is arranged coiling the magnet obverse faces in right-hand turns from one end to the other end of the bar magnets in the lengthwise direction, and at the same time, the plurality of magnets onto which the wire is wound are disposed to form a tubular hollow with the N-pole faces and the S-pole faces adjoining in alternation, and the shaping support material is put on the outside thereof. The method of using the physical-health tuning means is by setting on the body that end of the physical-health tuning means at which, when a bearing compass is brought near the physical-health tuning means along a straight line parallel to its lengthwise direction and passing the center point of the tubular hollow, the compass swings strongly in its N-pole direction.

In the alternative embodiment noted in the foregoing, in which bigger-sized bar magnets are used such that the shaping support material is unnecessary, the force of magnet attraction is so strong that using a compass as just described is not useful for determining which end of the physical-health tuning means is effective. Instead, persons sensitive enough can feel either comfort or discomfort depending on whichend of each magnet is placed on the person's head, either before or after the magnet is coiled. Of course, the end(s) lending a comfortable feeling form the end of the physical-health tuning means set on the body for tuning a person's health.

Conceivable reasons why a person's physical health might become out of sorts due to exposure to electromagnetic waves are as follows.

In their healthy state, red blood cells in the human body carry a positive charge, as do the inner walls of the blood vessels. Accordingly, red blood cells flow smoothly along the blood vessel inner walls, such that physical health is maintained.

Electromagnetic waves change the air into positive ions. Then due to the increase of positive ions in the atmosphere, positive ions infiltrate the human body's electrical system, increasing positive ions within the body.

Consequently, electromagnetic waves send positive ions onto the outer walls of blood vessels, and the blood vessel inner walls reversely become charged with negative ions. Thus, the flow of positively charged red blood cells within the blood vessels is impaired, putting physical health out of sorts.

Furthermore, inserting platinum, crystal fibers, rhombohedral system crystalline substances (for example, minerals such as crystal and cryptocrystalline quartz, graphite, black lead, calcite, feldspar, amethyst, tourmaline, lapis lazuli; as well as coal and charcoal), or calciferous substances (corals, conches, and the like) into the tubular hollow in a physical-health tuning means in terms of the present invention, will heighten the effectiveness of the physical-health tuning means. Objects containing rhombohedral system crystalline substances or calciferous substances may also be inserted. For example, because graphite is a raw material in pencils, inserting pencil(s) into the physical-health tuning means can heighten the physical-health tuning means effectiveness.

Further, a graphic recording medium on which is recorded as a picture a physical-health tuning means into which an insertion body derived from platinum, crystal fibers, a rhombohedral system crystalline substance or calciferous substance is inserted ("insert-carrying physical-health tuning means" hereinafter), is effective in tuning physical health, as, otherwise, are prints from the graphic recording medium. Likewise effective, furthermore, is a graphic recording medium on which the same picture on the just-noted graphic recording medium is recorded repeatedly superimposed; or otherwise prints therefrom. Also effective in tuning physical health are acoustic recording media on which is recorded sound that is issued by a physical-health tuning means into which an insertion body is inserted; and further, acoustic recording media on which the same sound on the just-noted recording medium is recorded repeatedly superimposed.

The method as described earlier of setting the physical-health tuning means on the affected area is a basic use method, but alternatives are a method of viewing pictures recorded on graphic recording media (including those on which the same picture is superimposed), or prints from the graphic recording media, and a method of listening to sounds recorded on acoustic recording media (including those on which the same sound is superimposed). Further, installing graphic recording media and prints therefrom, or sound storage media, in the four corners of a room, and staying in the room can yield effectiveness in tuning physical health.

In yet another aspect of the present invention, a physical-health tuning means is heightened in physical health tuning effectiveness by repeating operations that include: (a) recording as a picture an insert-carrying physical-health tuning means, onto a graphic recording medium and preparing a print therefrom, or superimposing the picture recorded on the given graphic recording medium at least once onto the graphic recording medium, and preparing a print therefrom; (b) drawing out the insertion body from the insert-carrying physical-health tuning means, and after wrapping the insertion body with the print, burning the print, or otherwise burning the print nearby the insertion body; and (c) reinserting the insertion body.

Further, by disposing an insert-carrying physical-health tuning means (including graphic recording media, prints therefrom, or sound storage media) nearby an electric switchboard physical health can be tuned utilizing electric appliances that use electric power supplied from the electric switchboard. What is more, keeping foodstuffs in a refrigerator that uses this electric power extends their shelf life.

Moreover, disposing an insert-carrying physical-health tuning means oriented toward an internal combustion engine, or else sticking fast a picture recording medium, a print therefrom, or an acoustic storage medium to the fuel tank can improve the engine's rate of fuel consumption.

Further, by immersing the insert-carrying physical-health tuning means in water, the water quality can be purified. Putting a foregoing insertion body into a bathtub and bathing boosts blood circulation and prolongs post-bathing warmth.

From the following detailed description in conjunction with the accompanying drawings, the foregoing and other objects, features, aspects and advantages of the present invention will become readily apparent to those skilled in the art.

DETAILED DESCRIPTION

Modes of Embodying the Invention

Figure 1:
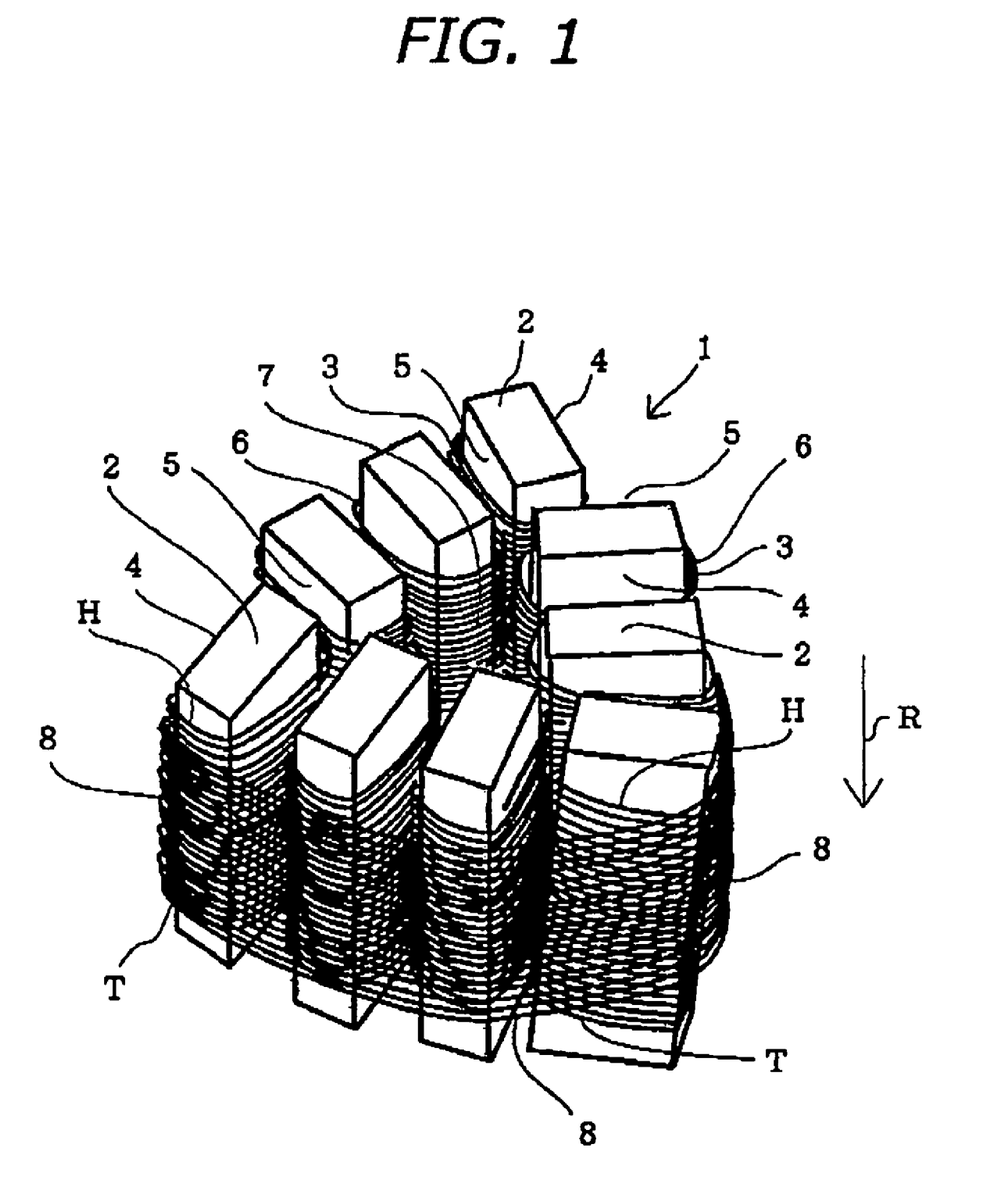
FIG. 1 is an oblique schematic view of one embodiment of a physical-health tuning means in terms of the present invention.
Figure 2:
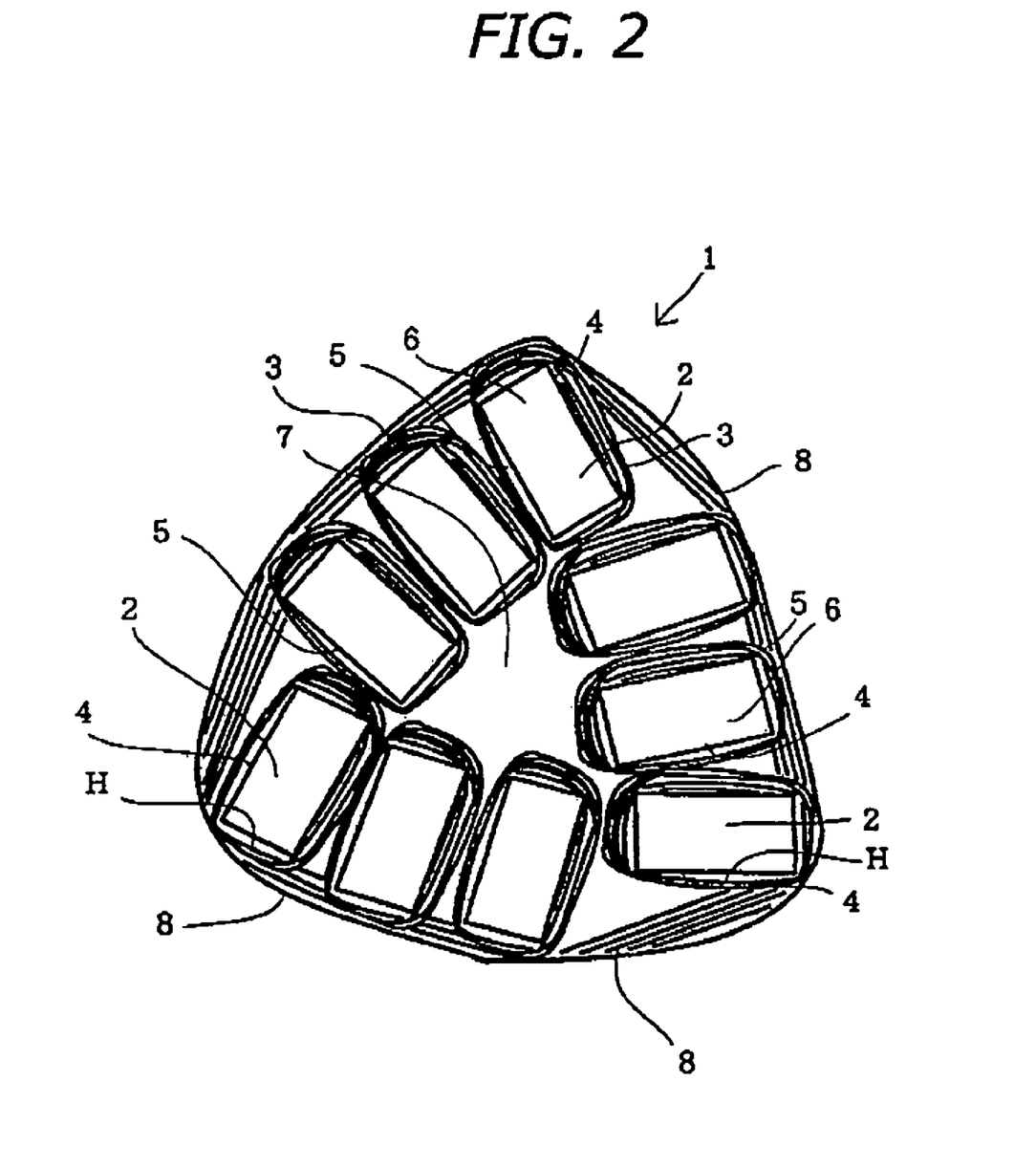
FIG. 2 is a schematic plan view of the physical-health tuning means in FIG. 1.
Figure 3:
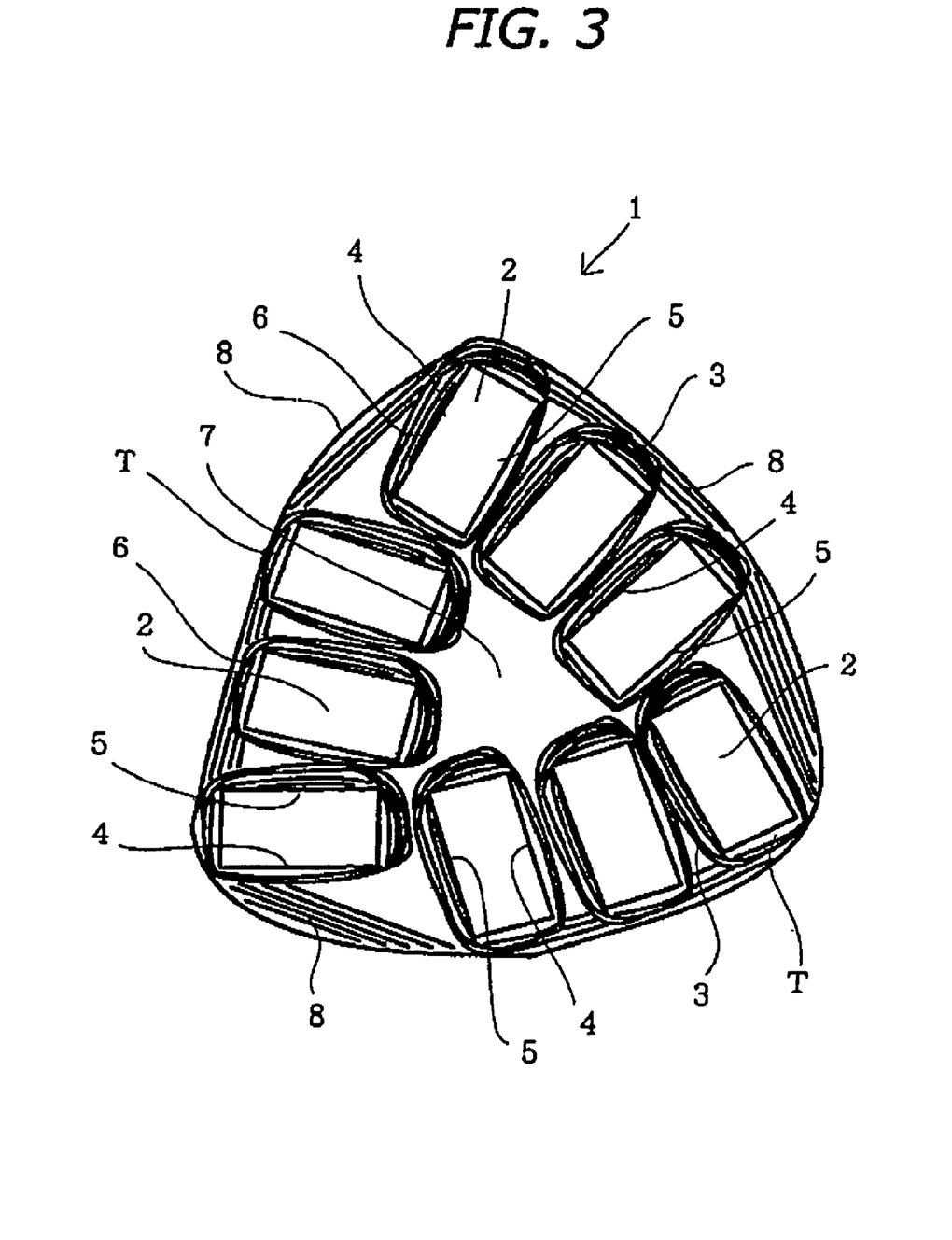
FIG. 3 is a schematic bottom-face view of the physical-health tuning means in FIG. 1.

A physical-health tuning means of the present invention will be explained based upon the drawings. FIG. 1 is an oblique schematic view of a physical-health tuning means 1 in terms of the invention; FIG. 2 is plan view of the same schema; and FIG. 3 is bottom-face view of the same schema.

In the figures, 2 are plate magnets, and 3 is wire made of copper that is non-magnetic yet electroconductive, wound onto the magnets 2 along their lengthwise direction R, coiled in right-hand turns from one end H to the other end T in the lengthwise direction R of the magnets 2, whose obverse faces 4 are N-poles and whose reverse faces 5 are S-poles. The one end H where the windings begin and the other end T where the windings end are both in places slightly inward of either end lengthwise along the magnets. Nine wire-wound magnets 6, with the N-pole faces N adjoining the S-pole faces Sin alternation, are arranged to form a tubular hollow 7 generally triangular in cross-section.

A construction arranged as in the foregoing, on the outer side of which copper wire 8 is put as a shaping support material, is a physical-health tuning means of the present invention.

A method of manufacturing a physical-health tuning means of the present invention will be explained based on FIG. 4.

Figure 4A:
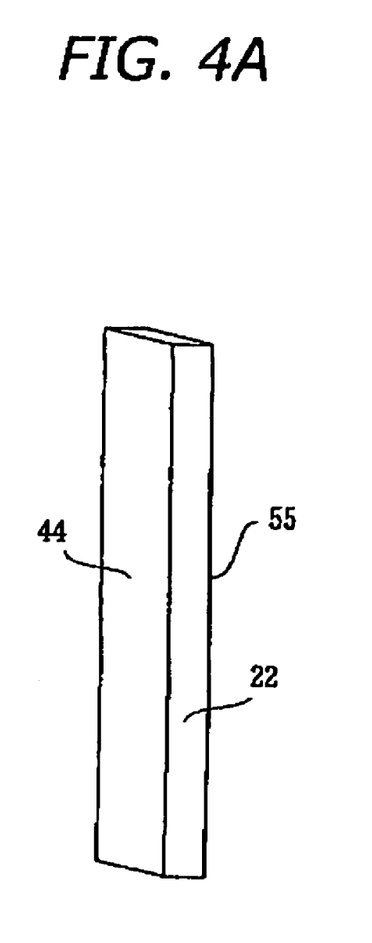
FIG. 4A is an oblique schematic view of a plate magnet composing a physical-health tuning means in terms of the present invention.

FIG. 4A is of a plate magnet 22 with which a physical-health tuning means in terms of the invention is configured, and its obverse side 44 running lengthwise is the N-pole, while the reverse side is the S-pole. FIG. 4B is of a wire-wound magnet 66 onto which wire 33 that is non-magnetic yet electroconductive is wound, coiling in right-hand turns onto the obverse face of the plate magnet 22.

Figure 4B:
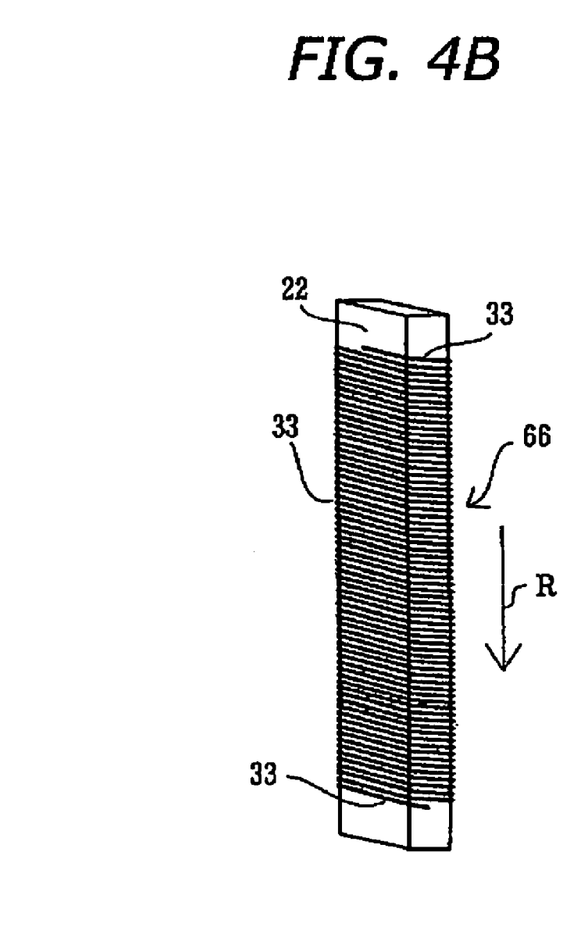
FIG. 4B is an oblique schematic view of a wire-wound magnet composing a physical-health tuning means in terms of the present invention.

To manufacture the physical-health tuning means in FIG. 1 nine wire-wound magnets 66 are prepared by readying nine plate magnets 22, and winding the non-magnetic yet electroconductive wire 33 onto the obverse face of the plate magnet 22, coiling in right-hand turns, along the lengthwise direction R as shown in FIG. 4B. Herein, winding the wire 33 onto the obverse face of the plate magnet 22, coiling in right-hand turns as shown in FIG. 4B, means winding on the wire 33 counterclockwise in coils along the lengthwise direction R from the upper-end of the magnet longitudinally to the lower-end of the magnet. Subsequently, the wire-wound magnets 66 are grouped with their N-poles and S-poles adjoining. Consequently, a wire-wound magnet assembly (not illustrated) having a tubular hollow 7 generally triangular in cross-section as shown in FIGS. 1, 2 and 3 is made. As is, the form of this assembly would break apart on receiving exterior force and would not be able to retain its tubular hollow. To prevent this, the physical-health tuning means is completed by putting the shaping support material around the outside of the assembly. As long as the shaping support material maintains the tubular hollow in, and retains the form of, the physical-health tuning means, the shaping support material, no matter what the substance, may be either tubiform, filamentous or strap-like in form. From the standpoint of shape-retention and effective reinforcement, however, wire manufactured of metal that is electroconductive is, ordinarily, used.

The following method may be adopted as a way of tuning physical health using the physical-health tuning means.

The end of the physical-health tuning means where, when a bearing compass is brought near the physical-health tuning means along a straight line passing through the center point of the tubular hollow in, and longitudinally parallel to, the physical-health tuning means, the N-pole direction is indicated more strongly is set on a person's body.

The way the physical-health tuning means is set on a person's body is by direct contact, resting it on the body for five minute durations in regions such as on top of the head, the back of the head, the forehead, the backs of the legs, the eyelids, the arms. By continuing use even after five minutes have elapsed the feeling will be even better, and sometimes the person falls asleep just like that. Nevertheless, resting on a person's body the end of the physical-health tuning means where the N-pole direction is indicated more weakly is not effective.

Figure 5A:
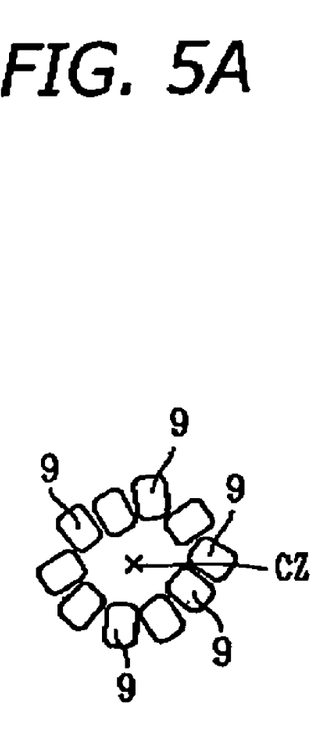
FIGS. 5A and 5B are schematic plan views respectively illustrating (omitting wire and shaping support material) other examples of a physical-health tuning means in terms of the present invention.
Figure 5B:
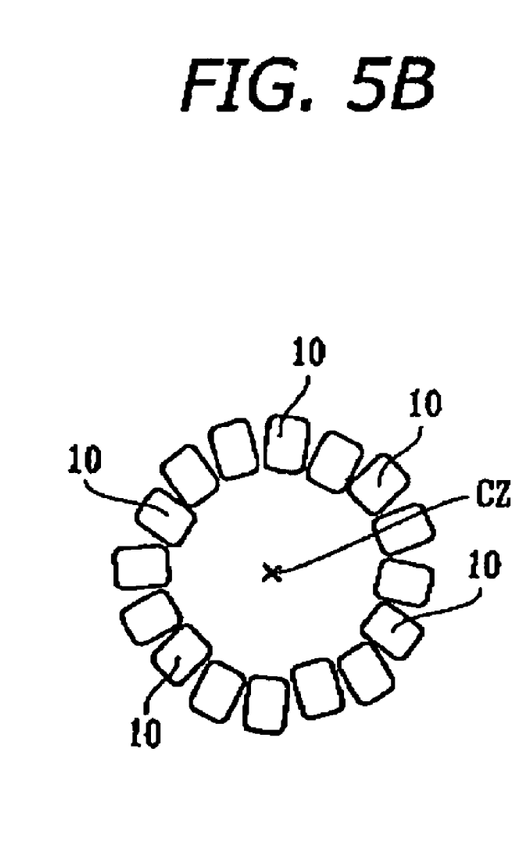

Another mode of embodying a physical-health tuning means in terms of the present invention is indicated in FIGS. 5A and 5B. The wire and the shaping support material are omitted and only the arrangement of the magnets is shown in FIGS. 5A and 5B, which are plan views in outline of physical-health tuning means using ten plate magnets 9—FIG. 5A—and sixteen plate magnets 10—FIG. 5B. Herein, the X s CZ in FIGS. 5A and 5B are centers zero of the tubular hollows in the physical-health tuning means.

Figure 6:
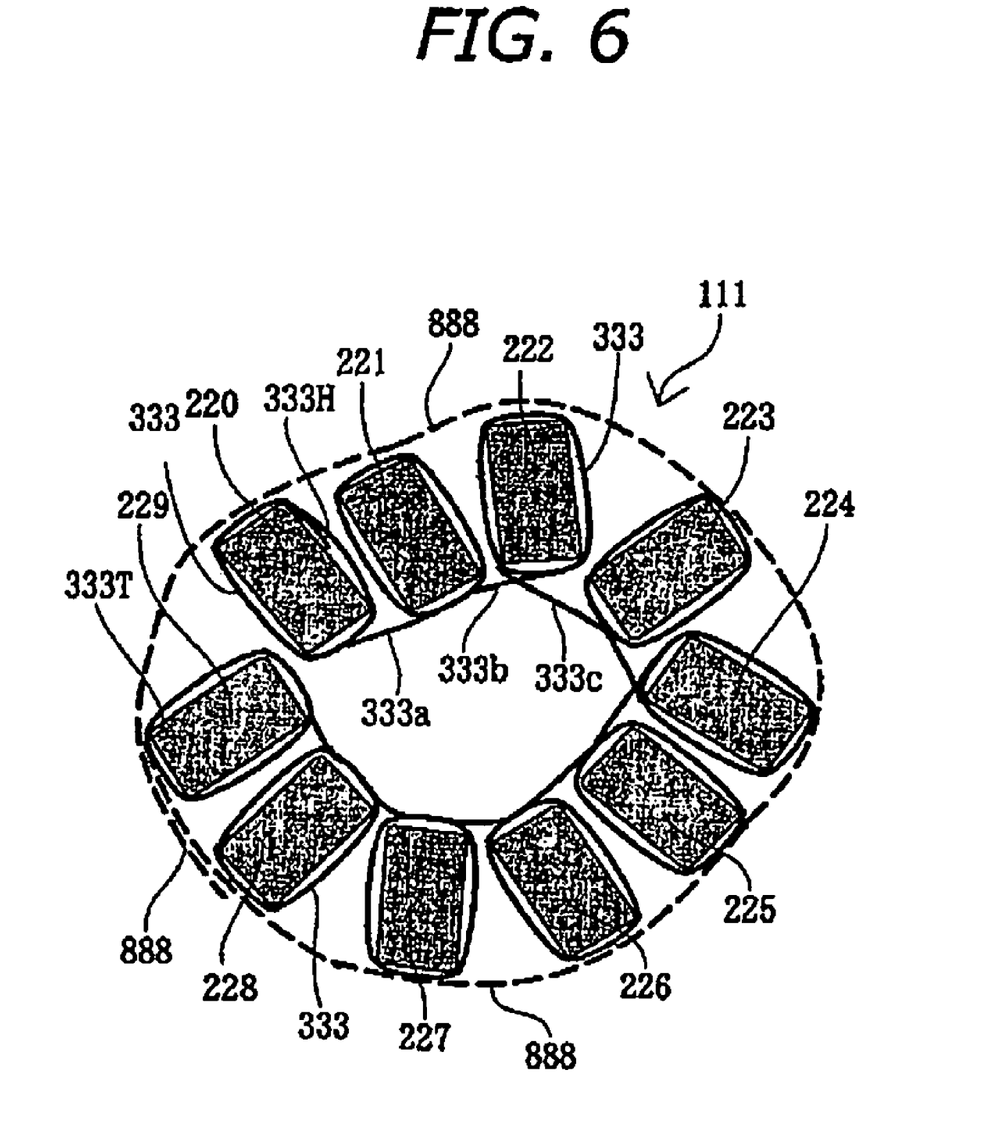
FIG. 6 is a schematic plan view of a physical-health tuning means, for outlining a method in terms of the present invention of manufacturing the physical-health tuning means.

A method of manufacturing a physical-health tuning means, in another embodiment in terms of the present invention, will be explained based on FIG. 6. FIG. 6 corresponds to FIG. 5A of a physical-health tuning means in terms of the present invention. Whereas FIG. 5A omits, FIG. 6 shows the wire and the shaping support material, however.

That is, in the FIG. 6 instance, a single strand of wire is used, by which the shaping support material, continuous with the wire has the same non-magnetic yet electroconductive properties. Nevertheless, to clarify the configurational positions of the two, for convenience's sake the wire is indicated by a solid line and the shaping support material by a broken line.

In FIG. 6, 111 is a physical-health tuning means; 220 sequentially through 229 are plate bar magnets; 333 is wire on the magnet obverse faces from one end to the other of the bar magnets longitudinally, the wire being arranged coiling in right-hand turns; and 888 is the shaping support material. The wire 333 and the shaping support material 888 are a single continuous strand that is non-magnetic yet electroconductive, as just described.

In manufacturing the physical-health tuning means 111 of FIG. 6, wire is wound onto the first plate bar magnet 220 among the plate bar magnets 220–229, longitudinally from one end to the other of the magnet obverse face to form right-winding coils.

Herein, 333 H in FIG. 6 is where the winding starts when winding the wire 333 onto the obverse face of the plate bar magnet 220.

Subsequently, the portion of the wire where the windings onto the foregoing wire-wound magnet conclude is wound onto the second plate bar magnet 221 longitudinally from one end to the other so that the wire forms right-winding coils on the magnet obverse face.

Herein, 333*a* in FIG. 6 is the portion that transitions from plate bar magnet 220 to plate bar magnet 221.

Subsequently, the portion of the wire where the windings onto the second wire-wound magnet conclude is wound onto the third plate bar magnet 222 longitudinally from one end to the other so that the wire forms right-winding coils on the magnet obverse face.

Herein, 333*b* in FIG. 6 is the portion that transitions from plate bar magnet 221 to plate bar magnet 222.

Further then, the portion of the wire where the windings onto the third wire-wound magnet conclude is wound onto the fourth plate bar magnet 223 longitudinally from one end to the other so that the wire forms right-winding coils on the magnet obverse face.

Herein, 333*c* in FIG. 6 is the portion that transitions from plate bar magnet 222 to plate bar magnet 223.

Wire is likewise wound onto the remaining bar magnets 224 through 229 in turn.

Subsequently, a cylindrical assembly is prepared by arranging the ten wire-wound magnets to adjoin with the N-pole faces alternating with the S-pole faces, to form a tubular hollow.

Herein, after winding the wire from one end to the other of the first bar magnet longitudinally, so as to from coils right-winding on the magnet obverse face, when winding onto the second bar magnet the portion where the winding onto the first concludes, attention should be given to the following.

Namely, the length of the transitioning portion 331 between the first bar magnet 220 and the second bar magnet 221 is taken into consideration while the companion faces of the first and second bar magnets 220 and 221 that mutually attract magnetically are put next to each other. Also, when wire is wound onto the second bar magnet 221, the first bar magnet 220 immediately adjoining would encumber the wire-winding operation, and therefore the wire is wound on with the first bar magnet 220 and the second bar magnet 221 in separated positions so as not to hinder the wire-winding operation. For example, the wire may be wound on with the first bar magnet 220 and the second bar magnet 221 arranged not side by side, but one behind the other. Attention likewise should be given thereafter in winding the wire onto the remaining bar magnets 222 through 229 sequentially.

Subsequently, if to formatively support the cylindrical assembly the wire 888 is to be wound in coils onto the assembly girth, a physical-health tuning means of the present invention is completed by winding the wire 888 onto the cylindrical assembly longitudinally from one end to the other in coils around the girth, with 333 T, where the wire windings on the bar magnet 229 conclude, as the winding start.

EMBODIED EXAMPLES

In the following, use efficacy on persons having symptoms thought to be the influence of electromagnetic waves issuing from electronic devices was apparent with a physical-health tuning means of FIG. 1, 10 mm×20 mm in cross-sectional form, 60 mm in length, in which are used: plate bar magnets, running the lengthwise direction, whose obverse sides are N-poles and whose reverse sides are S-poles; copper filament 1.2 mm in thickness for the wire; and copper wire 1.2 mm in thickness for the shaping support material. Herein, when a bearing compass is brought near the physical-health tuning means along a straight line passing through the center point of the tubular hollow 7 in, and longitudinally parallel to, the FIG. 1 physical-health tuning means, the face on the end where the N-pole direction is indicated more strongly, which is the underside face shown in FIG. 3, is set on a person's body.

Trial Subject A's Case: Surrounded by personal computers in the workplace, this person also uses a personal computer daily. Had been out of sorts ever since coming to use a personal computer at work, and recently had had an ongoing slight fever.

The physical-health tuning means was rested both about the brow of the head, and on the underside of the arches of the feet. As a result at about five minutes' elapsed time post-use, coolness and calmness were felt in the areas where applied, and by the slight fever going away physical health got better.

Trial Subject B's Case: Uses a personal computer daily in the workplace. Annoyed by discomfort until then from the kidney swelling on one side of the body; and had been feeling a heavy sensation in the liver ever since coming to use a personal computer.

The physical-health tuning means was rested both about the brow of the head, and on the underside of the arches of the feet. As a result at about five minutes' elapsed time post-use, coolness and calmness were felt in the areas where applied, along with which the foregoing symptoms for the most part did not appear.

Trial Subject C's Case: Oversensitive to the cold, susceptible to air conditioning, uses a personal computer in the workplace.

The physical-health tuning means was rested both about the brow of the head, and on the underside of the arches of the feet. As a result at about four minutes' elapsed time post-use, the body temperature was felt to warm, and the body was felt relaxing.

Trial Subject D's Case: Uses a mobile telephone and a personal computer. Bothered by constant stiffness in the left shoulder.

The physical-health tuning means was rested both on the left shoulder, and around the anklebone on the outside of the right foot. As a result at about four minutes' elapsed time post-use, the foregoing symptoms went away.

Trial Subject E's Case: Uses a mobile telephone and a personal computer. Bothered by eye fatigue.

The eyes were closed, and the physical-health tuning means was rested on the eyelids. As a result at about four minutes' elapsed time post-use, the foregoing symptoms for the most part were no longer felt.

Trial Subject F's Case: Tumbled from the top of a stepladder, spraining the left elbow; also felt pain in the shoulders.

The physical-health tuning means was rested on the affected areas. As a result at about ten minutes' elapsed time post-use, warming around the affected areas was felt, and the foregoing symptoms for the most part were no longer felt.

In situations in which previous symptoms in the of trial subject A, B, C, D, and E cases thereafter reoccurred, applying a physical-health tuning means of the present invention improved in the foregoing manner health physically out of sorts.

Furthermore, even in a case in which health was not physically out of sorts due to electromagnetic waves, as with trial subject F, it was found that the effectiveness of a physical-health tuning means of the present invention could be affirmed.

At the present stage, the following is conceivable as a reason why a physical-health tuning means of the present invention is effective with regard to clearing up health physically out of sorts.

Through application of a physical-health tuning means of the present invention, a reducing action works on positive ions increased within the human body due to exposure to electromagnetic waves. Consequently, the inner walls of blood vessels reversed by exposure to electromagnetic waves—blood vessel inner walls charged with negative ions—go essentially into a positively charged state. Consequently, red blood cells flow smoothly along the blood vessel inner walls, which turns out to restore wellness.

Herein, where a physical-health tuning means of the present invention is to be used, it is better utilized in a location endowed with a natural environment, such as a log house for example. Use in locations where electromagnetic waves are flitting about, in densely built metropolitan areas for example, dilutes the effectiveness. In such instances, clutching a shell-like natural substance in the bare hand and using a physical-health tuning means of the present invention can increase effectiveness.

Further, inserting an insertion body derived from platinum, crystal fibers, rhombohedral system crystalline substances or calciferous substances into a physical-health tuning means of the present invention makes heightening physical health tuning effectiveness possible. Minerals such as crystalline and cryptocrystalline quartz, graphite, black lead, calcite, feldspar, amethyst, tourmaline, and lapis lazuli, as well as coal and charcoal, are available as rhombohedral system crystalline substances; and corals, conches, and the like are available as calciferous substances. Similar effects may be gained with objects containing these substances (pencils, to give an example, in which graphite is a raw material) as the insertion body. The insertion body may be also objects containing these substances (pencils, to give an example, in which graphite is a raw material), to yield similar effects.

Figure 7:
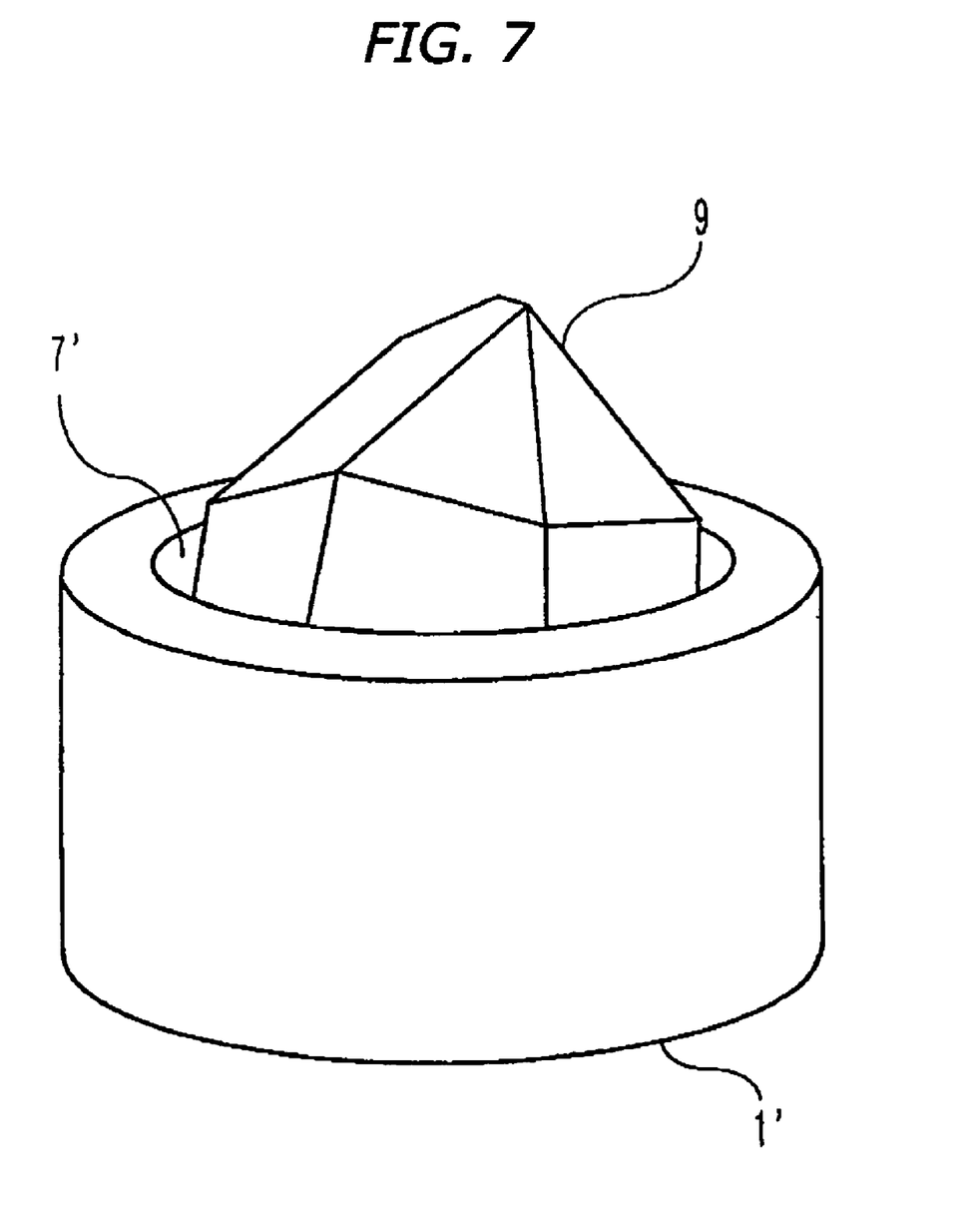
FIG. 7 is an oblique overview diagram of a physical-health tuning means into which a quartz crystal is inserted (an insert-carrying physical-health tuning means) in terms of the present invention.

FIG. 7 is an example using crystalline quartz 9 as an insert, wherein the crystalline quartz 9 is inserted into the tubular hollow 7" in a physical-health tuning means 1". It should be understood that the physical-health tuning means 1" is illustrated in FIG. 7 as a cylindrical outline, with the individual plate magnets, the wire, and the shaping support material omitted. Further, the insert should be as close-fitting as possible put into the tubular hollow 7"; the closer the fit, the greater the effectiveness.

The physical-health tuning means 1" is 7 mm×10 mm in cross-sectional form, 50 mm in length, in which are used: 21 plate bar magnets arranged cylindrically running the lengthwise direction, whose obverse sides are N-poles and whose reverse sides are S-poles; copper filament 1.2 mm in thickness for the wire; and copper wire 1.2 mm in thickness for the shaping support material. The tubular hollow 7" is thus a cylindrical form approximately 70 mm in diameter.

Methods of using the physical-health tuning means into which an insert is inserted are also in the manner described in the foregoing. That is, physical health may be put in order by setting the means directly on the affected area.

Further, without resting the means directly on the affected area, physical health tuning effects may be obtained from media onto which an insert-carrying physical-health tuning means is recorded as a picture, or alternatively, media onto which sound issuing from the insert-carrying physical-health tuning means is recorded.

Ways of recording an insert-carrying physical-health tuning means as a picture may be methods based either on cameras (those that work by conventional optics), digital cameras or video cameras. Accordingly, appropriate graphic recording media are: for cameras, film; for digital cameras, electronic storage media such as floppy disks, MOs and CD-ROMs; and for video cameras, video tape. Setting these graphic recording media on the affected areas yields physical health tuning effects.

Prints reproduced from the foregoing recording media are also effective. That is, there are physical health tuning effects from photographs, if the recording medium is a camera; from prints made by printer, if a digital camera; and from prints made by a still-picture video printer, if video tape.

Physical health tuning effects are thought to persist once an insert-carrying physical-health tuning means is recorded as a picture(s) onto a graphic recording medium. In particular, the graphic recording medium may be a floppy disk, a MD (minidisk) or videotape overwritten as much as possible. Initially, an insert-carrying physical-health tuning means is recorded onto such graphic recording medium, and by thereafter superimposing the same picture, efficacy may be further increased.

Utilizing personal computer image editing software is a possible method of superimposing images. Initially, an image file digitized with, e.g., a digital camera is opened with an image-editing application, the image is copied and pasted in at least a single-time superimposition, and the image file is saved. There are increased physical health tuning effects with an image file prepared in this way. Further, if a favorite image is superimposed onto such image file, and used as so-called wallpaper in a personal computer, the personal computer user may use a favorite image as wallpaper while sustaining physical health tuning efficacy.

Tape recorders and minidisk recorders are ways for recording sound issuing from insert-carrying physical-health tuning means. Cassette tape and minidisks would be appropriate sound recording media.

In instances of recording as sound also, physical health tuning effects are thought to persist. In particular, the acoustic recording medium may be cassette tape or a minidisk overwritten as much as possible. Initially, sound issuing from an insert-carrying physical-health tuning means is recorded onto such acoustic recording medium, and thereafter the same sound may be superimposed. An acoustic recording medium onto which the same sound is superimposed in this way will have increased efficacy.

Of course, viewing pictures recorded onto graphic recording media (including those onto which the same image is superimposed), and prints therefrom yields physical health tuning efficacy; and listening to sound recorded onto acoustic recording media (including those onto which the same sound is superimposed) yields physical health tuning efficacy.

By disposing a graphic recording medium and prints therefrom, or an acoustic recording medium, in the four corners of a room and staying in the room, physical health tuning effects will appear.

Increasing physical health tuning efficacy can be by other methods as well.

Namely, it may be realized with a physical-health tuning means as claimed in another aspect of the present invention, by repeating the following operations: (a) recording as a picture an insert-carrying physical-health tuning means, onto a graphic recording medium and preparing a print therefrom, or superimposing the picture recorded on the given graphic recording medium at least once onto the graphic recording medium, and preparing a print therefrom; (b) drawing out the insertion body from the insert-carrying physical-health tuning means, and after wrapping the insertion body with the print, burning the print, or otherwise burning the print nearby the insertion body; and (c) reinserting the insertion body.

This will be explained specifically. First, in (a) as described earlier, using image-editing software, an image of an insert-carrying physical-health tuning means is superimposed at least one time, and is materialized by printing out the superimposed image. In (b), the insertion body is drawn out, and the print is burned nearby the insertion body. Alternatively, the print may be burned after wrapping the insertion body with the print. In (c), the insertion body is inserted again into the physical-health tuning means. By repeating operations (a)(c) a number of times, physical health tuning efficacy will increase. Of course, by recording an insert-carrying physical-health tuning means as a picture onto a graphic recording medium, there are also physical health tuning effects with prints of the picture.

Definite physical health tuning effects from an insert-carrying physical-health tuning means on which, repeated five times, the above-noted operations (a)(c) were carried out, while image superimposition in (a) was done five times.

Additionally, a print as prepared in (a) above may be burned in the vicinity of malted rice, leavenings such as yeast, fermented soybeans and other foods containing the soy-fermenting bacteria in the Japanese food "natto," beer malt, malt, yogurt and other foods containing the milk-fermenting bacteria in yogurt. These foods may then be eaten for tuning physical health.

For tuning physical health, these foods may then be eaten or placed on the part of the body where one feels pain, is burned or feels out of sorts. For example, an aluminum sack containing dried beer malt can be set on a region of the body where one feels pain, is burned or feels out of sorts. Moreover, after burning prints as prepared in (a) above in the vicinity of crystals such as quartz, these likewise may be placed on the body. Burning prints as prepared in (a) above is assumed to enhance gravitational waves from the aforementioned foods and crystals nearby which the prints are burned.

Trial Subject G's Case: Trial subject G uses a personal computer regularly and therefore often feels stiffness in the shoulders. Upon using as so-called wallpaper on the personal computer an image in which, onto an image of an insert-carrying physical-health tuning means, recorded with a digital camera, another image is superimposed ("superimposed image" hereinafter) using image-editing software, fatigue was no longer felt even using the personal computer for a long time.

The implementation examples with trial subjects H-K shown below are examples in which prints from the superimposed image that trial subject G used were disposed in the four corners of a bedroom.

Trial Subject H's Case: Trial subject H suffered from constipation, but disposing the given prints in the four corners of a bedroom, saw rectification of the constipation symptoms.

Trial Subject I's Case: Trial subject I suffered from stomach pain, but the stomach pain symptoms were soothed.

Trial Subject J's Case: Trial subject J always went about weary, but has appeared effectively to recover from weariness.

Trial Subject K's Case: Trial subject K suffered from frequent urination during the night. Forced to urinate four, five, or more times in the middle of the night and not able to get into a comfortable sleep, but urination has been at the level of one time a night, making for restful sleep.

Efficacy for trial subjects G–K from the insert-carrying physical-health tuning means resembles physical health tuning effects due to gravitational waves. Accordingly, an insert-carrying physical-health tuning means (includes picture recording media and prints therefrom; "insert-carrying physical-health tuning vehicles" hereinafter) generating a greater amount of gravitational waves is presumed to have tuned the physical health of the trial subjects; but at present whether or not gravitational waves are generated by an insert-carrying physical-health tuning means cannot be confirmed. As technical background on gravitational waves as well as gravitons pertinent to the present invention in this respect, *Uchuugaku Joshou Gurabitonikkusu* (*Preface to Cosmology: Gravitonics*), by Hideo Seki, published by Kasoku Gakuen Ltd., Tokyo, 2000, is hereby incorporated in its entirety by reference. Likewise, chapters one and two of *Kokoro wa Uchuu no Kagami* (*The Mind is a Mirror of the Universe*), by Hideo Seki and Masando Sasakino, published by Seisei Ltd., Tokyo, 2000, are hereby incorporated by reference.

Furthermore, with regard to the method described above of burning a print made from a graphic recording medium onto which an insert-carrying physical-health tuning means according to the present invention is recorded as a picture, or a print made from the given graphic recording medium onto which the picture has been recorded superimposed at least once in the vicinity of the foods mentioned therein: The natural physical-health tuning effects due to gravitational waves from these foods are thought to be enhanced by thus burning a print nearby them.

Accordingly, if an insert-carrying physical-health tuning means is disposed nearby a place where electric-power lines are concentrated, by using electronic products with electric power that is propagated on electric power lines in which gravitational waves are dispersed from the electric-line concentration site, and supplied from the electric-power lines, physical health may be tuned. Electric-line concentration site may be electric switchboards and distribution switchboards, or simply a location where electric power lies are concentrated.

If the insert-carrying physical-health tuning means is to be used, a preferable method is to set it directly on the electric-line concentration site. If this is physically difficult, preferably it should be disposed by situating it as near as possible to the electric-line concentration site. The direction in which to situate the insert-carrying physical-health tuning means is with the longitudinal direction of the tubular hollow directed toward the electric-line concentration site.

Where graphic recording media, prints therefrom, and acoustic recording media are used, a preferable method is to stick them fast to walls nearby the electric-line concentration site. In this case, if the recording media and prints are stuck fast so that the direction normal to their surface is as directed as possible toward the electric-line concentration site, more effectiveness appears.

With such method, when televisions and computers are used, they may be used with images become sharp, and without feeling weary. Further, if used on heating appliances (electric heaters and electric stoves) and cooling appliances (air-conditioners), physical health tuning effects will show forth by being in the rooms in which the appliances are installed. Also, using a refrigerator with electric power supplied by the given method, and preserving food items in the refrigerator will lengthen shelf life. For example, bean sprouts that formerly could keep for only two days or so turned out able to keep seven days or more.

An insert-carrying physical-health tuning means is effective not only on the human body, but also on internal-combustion engines. By disposing an insert-carrying physical-health tuning means directed toward an internal-combustion engine (e.g., an automobile engine), or else sticking fast prints with its superimposed image to the fuel tank of an internal-combustion engine, the rate of fuel consumption of the internal-combustion engine may be improved.

Where an insert-carrying physical-health tuning means is to be used, a preferable method disposes it so that it rests directly on the internal-combustion engine. Since this normally is physically problematic, disposing it directed toward, from as near as possible to, the internal-combustion engine is desirable. The direction in which to situate the insert-carrying physical-health tuning means is with the longitudinal direction of the tubular hollow directed toward the internal-combustion engine. Further, where graphic recording media, prints therefrom, and acoustic recording media are used, a preferable method is to stick them fast to the fuel tank of the internal-combustion engine. Prints on paper or the like would be most suitable.

With respect to a domestic passenger car (gasoline vehicle), four sheets of prints with an above-described superimposed image were stuck fast to the fuel tank, and upon covering about 500 km, the rate of fuel consumption was from 9.34 km/l to 10.5 km/l, which was about a 13% improvement over what it had been. Furthermore, an insert-carrying physical-health tuning means was disposed directed toward the engine from the passenger seat, and upon covering about 500 km, the rate of fuel consumption was 10.85 km/l, which was about a 16% improvement.

Also with respect to a domestic passenger car (diesel vehicle), four sheets of prints with a superimposed image were stuck fast to the fuel tank, an insert-carrying physical-health tuning means was disposed directed toward the engine from the passenger seat, and upon covering about 500 km, a rate of fuel consumption that had been less than 10 km/l improved to 11.3 km/l. Acceleration was bodily sensed to have gotten better.

An insertion body is effective to improve water quality. For example, by immersing crystalline quartz described earlier into tap water, the water quality improves. To be specific, the water is characterized by a mellowness felt when it is drunk. Quantitatively, residual chlorine was confirmed with an assaying reagent (orthotolidine). Before immersing the crystalline quartz, the just-noted reagent was cast into the tap water, which changed into a pale yellow color, and the presence of residual chlorine was confirmed. After immersing and taking out the crystalline quartz, and casting in the reagent, however, the color did not change, which therefore confirmed that residual chlorine was eliminated. Herein, immersing the crystalline quartz for a 4 to 5 second extent purified the water well, in an extremely short time.

In addition, putting a foregoing insertion body into a bathtub and bathing is effective in boosting blood circulation and prolonging post-bathing warmth.

In the foregoing manner, the present invention offers a physical-health tuning means (a tuning means that adjusts/brings into harmony physical health by decreasing positive ions that have increased within the human body due to exposure to electromagnetic waves) that tunes physical health, in particular, improves physical health that is out of sorts due to harm from electromagnetic waves. The present invention at the same time offers methods of manufacturing and of using the physical-health tuning means. In addition, combined use with platinum, crystal fibers, rhombohedral system crystalline substances or calciferous substances makes it possible to heighten the physical health tuning efficacy further. Efficacy is not only on the human body, but also with regard to internal-combustion engines, making it possible to improve fuel consumption efficiency. Further efficacy has been in water purification, food preservation and bathing methods.

The invention claimed is:

1. An electrical-power-sourceless physical-health tuning means comprising:
    a plurality of bar magnets each of whose N and S poles runs lengthwise from end to end of the magnet, splitting the magnet by polarity longitudinally into N-obverse and S-reverse sides; and
    non-magnetic yet electroconductive wire arranged coiling each of said bar magnets in right-hand turns, with respect to the obverse face thereof from one end to the other end of the magnet in the lengthwise direction; said plurality of bar magnets being disposed in, and selected to have force of magnetic attraction strong enough to hold the magnets together in, a configuration forming a tubular hollow with the N-pole faces adjoining the S-pole faces in alternation.

2. A physical-health tuning means as set forth in claim 1, further comprising:
    a shaping support material put on the outside of said plurality of magnets onto which said wire is coiled.

3. A physical-health tuning means as set forth in claim 2, wherein said wire and said shaping support material are copper filament.

4. A physical-health tuning means as set forth in claim 2, wherein said wire and said shaping support material are a single continuous strand of non-magnetic yet electroconductive wire.

5. A method for tuning physical health utilizing a physical-health tuning means as set forth in claim 1, comprising:
    (a) bringing a bearing compass near either end of the physical-health tuning means along a straight line parallel to its lengthwise direction and passing through the tubular hollow center point;

(b) determining at which end of the physical-health tuning means the compass swings strongly in is north-pole direction;

(c) targeting at a human body the end of the physical-health tuning means determined according to said step (b).

6. A physical-health tuning means as set forth in claim 1, wherein an insertion body consisting of one selected from platinum, crystal fibers, a rhombohedral system crystalline substance, a calciferous substance, or a composition incorporating either a rhombohedral system crystalline substance or a calciferous substance is inserted into said tubular hollow.

7. A method of using a physical-health tuning means, wherein
a physical-health tuning means as set forth in claim 6 is set on a person's body.

8. A method of using a physical-health tuning means, wherein a physical-health tuning means as set forth in claim 6 is disposed in the four corners of a room.

9. An electrical-power-sourceless physical-health tuning means comprising:

a plurality of bar magnets each of whose N and S poles runs lengthwise from end to end of the magnet, splilling the magnet by polarity longitudinally into N-obverse and S-reverse sides; and non-magnetic yet electroconductive wire arranged coiling alternate ones of said bar magnets in right-hand turns, with respect to the obverse faces thereof, from one end to the other end of the magnets in the lengthwise direction, and on the remaining ones of said bar magnets said wire is arranged coiling the magnet obverse faces in left-hand turns from one end to the other end of the magnets in the lengthwise direction; said plurality of bar magnets being disposed in, and selected to have force of magnetic attraction strong enough to hold the magnets together in, a configuration forming a tubular hollow with the N-pole faces adjoining the S-pole faces in alternation.

10. A physical-health tuning means as set forth in claim 9, further comprising:

a shaping support material put on the outside of said plurality of magnets onto which said wire is coiled.

* * * * *